United States Patent [19]

O'Shannessy

[11] Patent Number: 4,874,813

[45] Date of Patent: Oct. 17, 1989

[54] PROTEINS BOUND TO A MARKER OR SOLID PHASE SUPPORT MATRIX USING A HYDRAZONE LINKAGE

[76] Inventor: Daniel J. O'Shannessy, 256 Congressional La. #T3, Rockville, Md. 20852

[21] Appl. No.: 12,456

[22] Filed: Feb. 9, 1987

[51] Int. Cl.$^4$ .......................... C07G 7/00; C08L 89/00
[52] U.S. Cl. .................................. 525/54.1; 530/395; 530/810; 530/811; 530/812; 530/813; 530/814; 530/815; 530/816
[58] Field of Search ............................ 525/54.1, 54.11; 530/333, 334, 395, 810, 811, 812, 813, 814, 815, 816

[56] References Cited

U.S. PATENT DOCUMENTS

| 3,873,514 | 3/1975 | Chu et al. ............................ 106/208 |
| 4,217,338 | 8/1980 | Quash .................................... 436/543 |
| 4,671,958 | 3/1982 | Rodwell et al. ....................... 424/85 |

FOREIGN PATENT DOCUMENTS 0088695 9/1988 European Pat. Off. .

OTHER PUBLICATIONS

Fan and Karush (1983) Fed. Proc. 42:930 (Abstract).
Ito et al. (1986) J. Biochem. 99:1267–1272.
Quash et al. (1978) J. Immunol. Meth. 22:165–174.
Chua et al. (1984) Biochem. Biophys. Acta 800:291–300.
O'Shannessy et al. (1984) Immunol. Lett. 8:273–277
O'Shannessy et al. (1985) J. App. Biochem. 7:347–355.
Bio-Rad Bulletin 1085 (1986) "Activated Affinity Supports: Affi–Gel 10 and 15".

*Primary Examiner*—John Kight
*Assistant Examiner*—Nathan M. Nutter
*Attorney, Agent, or Firm*—Townsend & Townsend

[57] ABSTRACT

A biological composition comprises a solid phase support matrix or marker molecule bound to protein, typically a glycoprotein such as an immunoglobulin through a linking group, spacer arm, and hydrazone group. The linking group is conveniently an ether linkage, while the spacer arm is a linear chain including six atoms, where at least one of the atoms is a tertiary amine which is protonated at a pH below about 8. The hydrazone is formed by reacting the solid phase or marker molecule having the linking arm and the spacer arm including a terminal hydrazide group with a glycoprotein oxidized to include a terminal aldehyde group. Immunological reagents prepared by linking an immunoglobulin (IgG) through a carbohydrate on the Fc or hinge regions have been found to provide very high binding capacity approaching the theoretical bivalent limit of two moles of bound antigen for every mole of bound immunoglobulin.

28 Claims, No Drawings

PROTEINS BOUND TO A MARKER OR SOLID PHASE SUPPORT MATRIX USING A HYDRAZONE LINKAGE

BACKGROUND OF THE INVENTION

1. Field of the Invention

The present invention relates generally to the binding of glycoprotein molecules to markers and supports. More particularly, the invention relates to a method for binding immunoglobulins through the carbohydrate moieties on their Fc regions using a hydrazone linkage.

Reagents prepared by binding immunoglobulin (Ig) molecules to a solid phase support matrix are useful in a variety of procedures, such as immunoassays, affinity chromatography, and the like. Generally, such reagents are used to bind and separate substances from a liquid phase, and it is desirable that the immunoglobulin retain as much of its native binding activity as possible. Immunoglobulins, such as IgG, are bivalent, and it is theoretically possible for each mole of bound immunoglobulin to bind up to two moles of its corresponding antigen or hapten. Moreover, immunoglobulins having a desired specificity are expensive to prepare, and it would be desirable to provide methods for their efficient binding to the solid phase without loss and/or inactivation during the binding process.

The most common method for binding immunoglobulins relies on derivatization of the amino groups in the Ig molecule. Although the method is simple and generally successful, the binding efficiency of the resulting product is usually low. Other conventional binding techniques include derivatization of the sulfhydryl groups in the Ig molecule and non-covalently coupling the antibodies through intermediate receptors, such as protein A or anti-$F_c$ antibodies. While such methods are suitable for particular applications, neither provide for efficient utilization of the Ig starting material and binding through the sulfhydryl groups results in a product having a low binding efficiency for the target antigen.

Recently, it has been proposed to bind imunnoglobulin molecules to other substances, such as labels and solid phase matrices, through the carbohydrate moieties on their Fc regions. Specifically, aldehydes are formed by selective oxidation of the carbohydrate, and the aldehydes reacted to form either (1) a Schiff base with amino terminal substances or (2) a hydrazone with hydrazide terminal substances. Theoretically, by binding through the Fc region of the Ig molecule, interference with the active Fab regions should be minimized and immunological binding should be maximized. Unfortunately, such binding procedures have not been demonstrated to provide the high binding efficiencies which are theoretically possible. Moreover, the procedures have generally provided for inefficient utilization of the starting Ig material, increasing the cost of the final product.

It would therefore be desirable to provide materials and methods for improving the binding efficiencies of Ig molecules when coupled to solid phase supports. In particular, it would be desirable to provide a method of binding Ig molecules through the carbohydrate groups on their Fc regions to a solid phase with high retention of binding efficiency and efficient utilization of the Ig starting material.

2. Description of the Background Art

Fan and Karush (1983) Fed. Proc. 42:930 (Abstract) briefly describes the binding of IgM to polyacrylic hydrazide agarose. Ito et al. (1986) J. Biochem. 99:1267–1272 describe the binding of disaccharides to epoxy-activated carriers with hydrazine hydrate and adipic acid dihydrazide. Quash et al. (1978) J. Immunol. Meth. 22:165–174 describe the binding of various substances, including IgG, to latex particles substituted with hydrazine groups. Aldehyde groups on the IgG were generated with sodium periodate and the aldehydes and hydrazine groups reacted to form hydrazone linkages. Chua et al. (1984) Biochem. Biophys. Acta 800:291–300 describes the binding of IgM to liposomes through hydrophobic hydrazides. O'Shannessy et al. (1984) Immunol. Lett. 8:273–277 describes the biotinylation of immunoglobulins through aldehydes provided on the carbohydrate moiety of the immunoglobulin and subsequent reaction with biotin hydrazide. European patent application No. 88,695 describes methods for binding immunoglobulins to a solid phase, such as an amine agarose, through aldehydes on the carbohydrate moieties of the immunoglobulin. The application also suggests the use of hydrazides for coupling carbohydrates.

SUMMARY OF THE INVENTION

Novel compositions comprise proteins, particularly glycoproteins and immunoglobulins, bound to a marker or solid phase support matrix through a linking group and a spacer arm. The linking group may be any conventional reactive functionality which can be introduced to the marker or solid phase support matrix. The spacer arm is a chain of at least six atoms, including at least one tertiary amine which is protonated at a pH of less than about 8. The remaining atoms in the chain will be carbon, oxygen, or nitrogen. The protein is bound through an aldehyde, typically introduced by oxidizing a carbohydrate moiety on a glycoprotein or immunoglobulin. The aldehyde is reacted with a hydrazide formed at the terminal end of the spacer arm attached to the marker or solid phase support matrix. In the case of immunoglobulins, the carbohydrate moiety is usually located on the Fc or hinge region, minimizing steric hindrance of the active Fab regions.

Compositions of the present invention are useful for various biological assays, procedures and processes, including affinity chromatography, immunoassays, DNA probes, separations, and the like. In the exemplary embodiment, a cross-linked agarose gel is derivatized with a conventional ether linking group and a spacer arm, as described above. The derivatized agarose is reacted with oxidized monoclonal antibodies specific for tissue plasminogen activator (tPA), and a binding efficiency in excess of 90% of theoretical is demonstrated.

DESCRIPTION OF THE SPECIFIC EMBODIMENTS

According to the present invention, compositions comprise proteins linked to a solid phase support matrix or marker molecule and have the following formula:

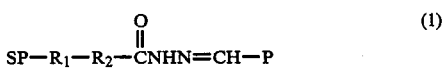

wherein:

SP is a solid phase support matrix or marker molecule;

$R_1$ is a conventional linking group which is introduced to the solid phase support matrix or marker molecule;

$R_2$ is a spacer arm as described in greater detail hereinbelow; and

P is the protein, usually a glycoprotein, more usually an immunoglobulin.

The solid phase support matrix may be any material conventionally used as a solid phase in immunochemical procedures, such as affinity chromatography and immunoassay. Suitable materials include cross-linked natural organic polymers, such as agarose, dextran, and cellulose; synthetic organic polymers, such as polymethacrylate and polystyrene, and inorganic polymers, such as silica, including both silica gel and crystalline silica. Natural biologic carriers, such as liposomes, proteins, and nucleic acids may also find use.

The solid phase support matrix material can be formed into a bead, particle, fiber, solid surface, membrane, soluble polymer, or the like. The form chosen will depend on the ultimate use of the Ig-bound solid phase matrix, with beads and gels being particularly useful for chromatographic separations, and solid surfaces and membranes being particularly useful for immunoassays.

A particular method for preparing agarose beads for affinity chromatography by cross-linking agarose with 1,3-dihalo-2-hydroxypropane is described in U.S. Pat. No. 3,873,514, the disclosure of which is incorporated herein by reference. Such derivatized agarose beads include an other linking arm ($R_1$), and are useful as a starting material for preparing the compositions of the present invention.

Marker molecules include a wide variety of substances which are desired to be covalently bound to proteins, glycoproteins, and immunoglobulins. Often, the markers will be detectable substances which serve as labels, such as enzymes, e.g., horseradish peroxidase; fluorescent compounds, e.g., fluorescein; bioluminescent compounds, e.g., luciferin, and the like. Marker molecules will also include nucleic acids, lectins, chelating agents, toxins, and intermediate binding molecules, such as biotin and avidin. This list is not intended to be exhaustive, and marker molecules will include virtually any molecule capable of covalent attachment to the linking group $R_1$, ranging in size from small molecules having a molecular weight below about 500 to macromolecules having a molecular weight above about 50,000.

Suitable linking groups $R_1$ will include a reactive functionality capable of binding the spacer arms $R_2$ of the present invention. Suitable reactive functionalities include esters, ethers, thiols, imidoesters, thioesters, thioethers, amides, hydrazones, and the like. The introduction of an ether linking arm onto an agarose gel solid phase support matrix is described in U.S. Pat. No. 3,873,514, previously incorporated herein by reference.

The compound employed as the spacer arm $R_2$ will be a chain having at least six atoms, frequently having at least eight atoms, and usually having at least ten atoms. The chain may have as many as 100 atoms, or more, usually having fewer than 50 atoms. At least one of the atoms in the chain is a tertiary amine which is protonated at a pH of less than about 8, frequently less than about 9, and often less than about 10. The remaining atoms of the chain will be carbon, oxygen, or nitrogen. The chain will usually include a backbone of at least six atoms arranged linearly, and may include various branches. The compound will usually include at least one amide group separated by a least one carbon atom from the tertiary amine, and a representative formula for the spacer arm is:

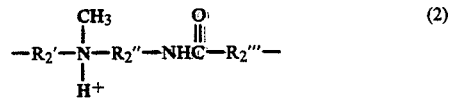

wherein $R'_2$, $R''_2$, and $R'''_2$ are aliphatic, having from one to six carbon atoms, usually being methylene, ethylene, propylene, or butylene groups, and may include one or more heteroatoms, usually from 0-2 primary or secondary nitrogens.

The preferred compound employed as the spacer arm has the formula:

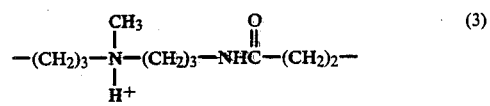

The proteins P will have aldehyde group(s) introduced to provide for binding to a hydrazide on the spacer arm, as described below. Conveniently, aldehydes may be introduced by coupling to available amine groups using suitable reagents, such as p-carboxylbenzene aldehyde, or by oxidizing the hydroxyl group on the benzenes of tyrosine. Other methods for introducing aldehydes are described in the scientific and patent literature.

Glycoproteins are polypeptides having at least one carbohydrate moiety attached to a serine, threonine, or asparagine residue. The glycoproteins of interest to the present invention may include one or more polypeptide chains, and will usually have a molecular weight in the range from about 10,000 to 500,000, more usually from about 25,000 to 300,000 with from about 2% to 40% of the weight being attributable to the carbohydrate. Such glycoproteins include antigens, antibodies, serum glycoproteins, enzymes, structural glycoproteins, and glycoproteins having other specialized sources, from a variety of sources, including plants, animals, bacteria and fungi.

Immunoglobulins (Ig), including both polyclonal and monoclonal antibodies, may be obtained commercially or produced by well known techniques. Conveniently, an antigen of interest is injected into a vertebrate to initiate an immunologic response. The animals are bled periodically, with successive bleeds having improved titer and specificity of the desired antibody. The antigen may be injected intramuscularly, intraperitoneally, subcutaneously, or the like, and a vehicle is usually employed, such as complete or incomplete Freund's adjuvant. If desired, monoclonal antibodies can be prepared according to the now classic teachings of Kohler and Milstein (1976) Eur. J. Immunol. 6:511–519.

The compositions according to the present invention are prepared by reacting oxidized immunoglobulins (having an aldehyde group formed at the terminal end of a carbohydrate) with the hydrazide-derivatized solid phase support matrix and marker molecules described above. The oxidized immunoglobulin may be formed by known chemical or enzymatic techniques under mild conditions chosen to avoid denaturing the immunoglobulin. Suitable chemical oxidizing agents include periodates, such as periodic acid and its salts. Suitable enzymatic oxidizing agents include galactose oxidase. The preferred technique is oxidation with sodium periodate (10 mM) at 0° C. for about 20 minutes.

The solid phase support matrix or marker molecule is derivatized with the linking arm $R_1$ by conventional techniques, with the particular technique chosen depending on the type of linking arm and the nature of the spacer arm ($R_2$). The preferred spacer arm (Eq. 3) may be linked to an agarose solid phase support matrix through the ether linkage as described in U.S. Pat. No. 3,873,514 by the following method.

A cross-linked agarose gel is reacted with 3,3'-diamino-N-methyldipropylamine (pH 6) at 25° C. After adjusting the pH to about 4.6, the gel is aminated with 1-ethyl-3-(3'-dimethylaminopropyl)-carbodiimide pH 4.6–4.8, by addition of 1N HCl. After washing in 1N NaOH and water, the gel is resuspended in water at pH 6–6.5 adjusted with NaOH. Succinic anhydride is reacted with the gel and the pH is maintained between about 5.5 and 7.0 by NaOH addition. The resulting triamine-succinate agarose gel may then be reacted with excess hydrazine hydrate to yield the hydrazine-derivatized solid phase support matrix of Eq. 3 described above. The triamine-succinate agarose gel of Eq. 3 may also be obtained commercially from Bio-Rad Laboratories, Chemical Division, Richmond, Calif., under the tradename Affi-Gel® 15.

The oxidized immunoglobulin and hydrazine-derivatized solid phase support matrix or marker molecule are reacted together under mildly acidic conditions (pH 4–5) for from 2 to 6 hours at room temperature. After reaction, the unreacted immunoglobulin is removed by rinsing with a buffer (pH 4–5). The immunoadsorbent may then be dried and stored or used immediately for immunochromatography or other immunological procedures.

An alternate preparation procedure is as follows. Poly(glydidyl methacrylate) reacted with sarcosine yields a polymer having the following subunits:

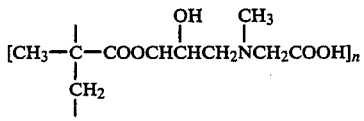

Conversion of the polymer with hydrazide yields:

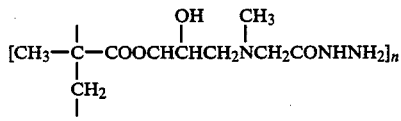

N-methyl-β-alanine nitrile or 4-(aminomethyl) butyric acid may be substituted for sarcosine in the above scheme. Substitution of the alanine would yield the corresponding secondary amines in the composition.

The following examples are offered by way of illustration, not by way of limitation.

EXPERIMENTAL

Materials and Methods 1. preparation of Affi-Gel® 10 and 15 Hydrazide

Affi-Gel® 10 and Affi-Gel® 15 (Bio-Rad Laboratories, Chemical Division, Richmond, Calif. 94804) are cross-linked agarose bead gels having N-hydroxysuccinimide esters at the terminal end of 6-atom and 11-atom spacer arms, respectively. The formula for each material, together with the delineation of the linking group and spacer arm, is as follows:

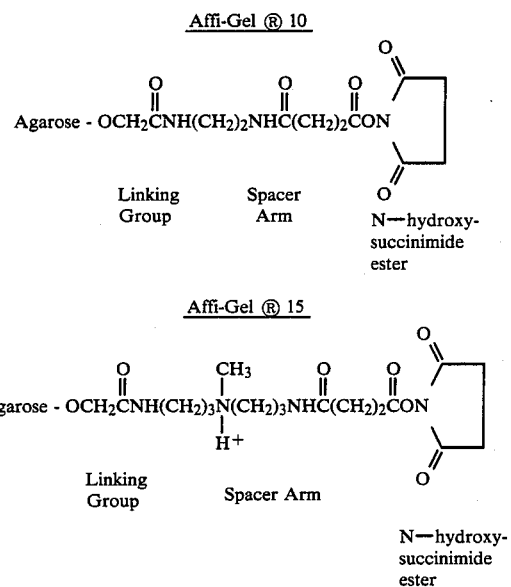

Affi-Gel® 10 or Affi-Gel® 15 (supplied in isopropanol) were brought to 25° C. and mixed on an orbital shaker. Hydrazine hydrate (2.0 ml) was added to 100 ml of the Affi-Gel® and allowed to react overnight at 4° C. with mixing. The gel was collected by gravity filtration using a plastic Bucher funnel (26 cm i.d.) and filtering cloth. The reacted gel was washed with 25 volumes of isopropanol followed by 90 volumes of buffer including 0.1 M sodium acetate, 0.15 M sodium chloride, 0.02% sodium azide, pH 5.5. Washings were repeated until the supernatant was negative when reacted with trinitrobenzenesulfonic acid (TNBS) as described by Inman et al. (1973) Immunochemistry 10:153–163. The gel was stored in the above buffer at 4° C. and retained binding activity for at least 6 months. For both Affi-Gel® 10 and Affi-Gel® 15, the reactive functionality substituted for the N-hydroxysuccinimide was as follows:

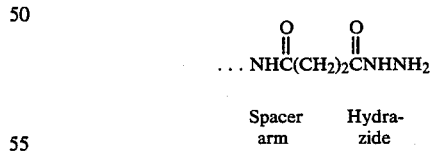

2. Periodate Oxidation of a Monoclonal Antibody

A monoclonal antibody (MAb) at 98% purity as judged by reducing SDS-PAGE was utilized in this experiment. The MAb was specific in immunoreactivity toward tissue plasminogen activator (tPA).

1.0 ml MAb solution (10mg) prepared in 0.1 M sodium acetate and 0.5M NaCl, pH 7.5, was diluted to 2.5 ml with 0.1M sodium acetate and 0.15M NaCl with 0.01M NaIO$_4$, pH 5.5. Both solutions contained 0.02% sodium azide. The periodate oxidation was allowed to proceed for 30 minutes at room temperature (23°–25° C.) in the dark with constant end-over-end mixing. To terminate the reaction, the entire volume was passed over a PD-10 (Pharmacia) gel filtration column previously equilibrated in sodium acetate-saline buffer, pH 5.5. The oxidized monoclonal antibody ($MAb_{ox}$) was eluted from the column in 3.5 ml 0.1 M sodium acetate with 0.15M NaCl, pH 4.5, in preparation for coupling.

3. Covalent Attachment of $MAb_{ox}$ to Affi-Gel ® 15 Hydrazide 3.0 ml $MAb_{ox}$ solution buffered at pH 4.5 was reacted with Affi-Gel ® 15 hydrazide previously equilibrated at pH 4.5. The coupling reaction was allowed to proceed for 4 hours at room temperature by end-over-end mixing in a sealed polypropylene column. At the end of the reaction period, the column was drained and extensively rinsed free of un-reacted $MAb_{ox}$ using the coupling buffer at pH 4.5. Finally, the column was re-equilibrated in phosphate-buffered saline, pH 6.8, for tPA antigen binding.

4. Binding and Release of tPA Antigen

Approximately 150 ml of dilute tPA antigen solution (0.1 mg/ml) prepared in 0.03M sodium tartrate with 0.3 M NaCl and 0.02% Tween ® 80, pH 5, was adjusted to pH 6.8. The pH 6.8 antigen solution was passed over the Affi-Gel ® hydrazide-$MAb_{ox}$ support (1.0 ml bed volume) at 5° C. over an 18–20 hour period. The column was rinsed free of unbound antigen by 100 ml PBS, pH 6.8.

Bound tPA antigen was then released from the column using 3.0 ml of 0.1M citric acid, pH 2. Analysis by high-performance size-exclusion chromatography indicatd that the antigen was released in the monomer form that is known to represent the active antigen. In a time course study, the antigen was found to convert slowly to dimer form (inactive) at pH 2.

5. Binding of Fetuin to Affi-Gel ® 10 and 15

50 mg fetuin (a bovine serum protein having 30 to 40% carbohydrate) in 2.5 ml 0.1M sodium acetate, 0.15M sodium chloride, 0.02% sodium azide, pH 5.5 was oxidized in the dark with 10 mM sodium periodate for 30 min. at room temperature. After this period, the oxidized fetuin was passed through a PD-10 (Pharmacia) gel filtration column equilibrated with the above buffer to remove residual periodate and to remove non-protein associated aldehydes produced during the oxidation. This solution was then added to 1 ml packed Affi-Gel ® Hydrazide (2,000 r.p.m. in a bench top centrifuge) equilibrated with the buffer described above. The gel was suspended using a pasteur pipette, then placed on an end-over-end mixer and allowed to react overnight at room temperature. The gel was sedimented by centrifugation and the supernatant removed. The gel was resuspended in 2 column volumes of 1M sodium phosphate, 1M sodium chloride, pH 7.4, and allowed to mix for 30 min. After centrifugation and removal of the supernatant, the washing procedure was repeated twice more. The supernatants were combined and the protein content measured by the method of Lowry et al. (1951) J. Biol. Chem. 193:165–175 using fetuin as the reference.

6. Binding of Horseradish Peroxidase to Affi-Gel ® 15

10 mg of horseradish peroxidase (HRP) was oxidized at room temperature for 30 min. with 10 mM sodium periodate at pH 5.5. Oxidized HRP was passed through a PD-10 (Pharmacia) gel filtration column equilibrated with acetate buffer, pH 4.5. The HRP solution was allowed to bind to 1 ml of Affi-Gel ® 15 for 2 hours at room temperature with end-over-end mixing. After this period, the gel was collected by centrifugation and the supernatant was shown to be devoid of protein by absorbance at 280 nm. The gel was then re-suspended and placed into a column. The Affi-Gel ® 15/HRP column was then eluted with 80×1 ml of 0.1M glycine/HCl pH 3.0. Fractions of 1 ml were collected into tubes containing 100 µl of 1M phosphate, 1M sodium chloride, pH 7.4 to immediately neutralize the eluant. 100 µl aliquots of each fraction were then assayed for HRP activity in microtitre plates using OPD as substrate. Results were compared with a standard curve of HRP treated in the same manner. Plates were read on an ELISA plate reader.

Results

The following analysis demonstrates that the Affi-Gel ® 15-hydrazide coupled $MAb_{ox}$ was able to bind and release tPA antigen at a binding efficiency of about 1.81 moles antigen per 1.00 moles of antibody which is 90.7% of the theoretical native antibody binding capacity.

| $MAb_{ox}$ Coupled (mg/ml gel) | $MAb_{ox}$ Coupling Efficiency (%) | tPA Antigen Released mgs/ml gel | Antigen Binding Efficiency (%) |
|---|---|---|---|
| 3.83 | 53.9%* | 3.01 | 90.7%** |

*Based on 2.37 mg/ml × 3.0 ml = 7.11 mg.
**1 mg antibody theoretically binds 0.867 mg antigen, which corresponds to a total theoretical binding capacity of 3.32 mg/ml.

In other experiments where this Mab was coupled to Affi-Gel ® 10, tPA binding of 20 to 38% was found. These results are similar to those reported in the literature for conventional binding techniques. The periodate oxidation of MAb and its coupling to supports having the tertiary amine-containing spacer arm of the present invention thus appear to offer some important advantages over conventional methodology.

Affi-Gel ® 15 having a tertiary amine in the spacer arm was found to bind fetuin both more rapidly and to a greater extent than Affi-Gel ® 10. In the procedure described above, Affi-Gel ® 10 was found to bind 32 mg/ml gel, while Affi-Gel ® 15 was found to bind 40 mg/ml gel. The time course for binding was as follows:

| Time (min.) | Affi-Gel ® 10 | | Affi-Gel ® 15 | |
|---|---|---|---|---|
| | Weight (mg) | Percent* | Weight (mg) | Percent* |
| 15 | — | — | 5.9 | 70 |
| 30 | 3.9 | 46 | 6.8 | 81 |
| 60 | 4.9 | 58 | 7.6 | 90 |
| 120 | 6.1 | 73 | 8.2 | 98 |
| 240 | 7.0 | 83 | 8.2 | 98 |

*Based on total amount bound.

An HRP column prepared as described above were tested for loss of glycoproteins. Elution of the HRP column showed an initial loss of HRP of approximately 100 ng per ml (OD approx. 0.2) for the first 20 ml. This value decreases to approximately 10–20 ng HRP/ml (OD approx. 0.05) for the remaining 60 ml (60 column volumes) of effluent. Therefore, there appears to be a slow but continuous leakage from the gel. Other evidence indicates that this is not a breaking of the hydrazone bond under these conditions but is most probably a breaking of the gel/spacer bond.

Although the foregoing invention has been described in some detail by way of illustration and example for purposes of clarity of understanding, it will be obvious

What is claimed is:

1. A composition having the formula:

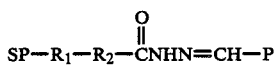

wherein:
SP is a solid phase support matrix or marker molecule;
R₁ is a linking group;
R₂ is a spacer arm having a chain of at least six atoms, with at least one of said atoms being a tertiary amine which is protonated at a pH less than about eight, and the remaining of said atoms being carbon, oxygen, or nitrogen; and
P is a protein.

2. A composition as in claim 1, wherein the solid phase support matrix is selected from the group consisting of agarose, dextran, cellulose, polymethacrylate, polystyrene, silica, protein, nucleic acid, and liposomes.

3. A composition as in claim 2, wherein the solid phase support matrix is in the form of a bead, particulate, fiber, solid surface, membrane, or soluble polymer.

4. A composition as in claim 1, wherein the marker molecule is selected from the group consisting of enzymes, fluorescent compounds, bioluminescent compounds, nucleic acids, lectins, toxins, linker molecules, and chelating agents.

5. A composition as in claim 1, wherein the protein is a glycoprotein linked through a carbohydrate moiety.

6. A composition as in claim 5, wherein the glycoprotein is an immunoglobulin linked through a carbohydrate moiety in the Fc or hinge region.

7. A composition as in claim 1, wherein the linking group is selected from the group consisting of ethers, esters, thiols, imidoesters, thioesters, thioethers, amides, and hydrazones.

8. A composition as in claim 1, wherein the chain is linear and includes an amide group separated by at least one carbon atom from the tertiary amine.

9. A composition as in claim 8, wherein the spacer arm has the formula:

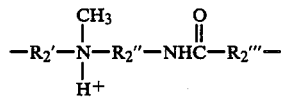

wherein:
R'₂, R''₂ and R'''₂ are aliphatic having from 1-6 atoms which may include from 0-2 primary or secondary nitrogen atoms.

10. A composition as in claim 9 wherein R'₂, R''₂ and R'''₂ are selected from the group consisting of methylene, ethylene, propylene, and butylene.

11. A composition as in claim 10, wherein the spacer arm is:

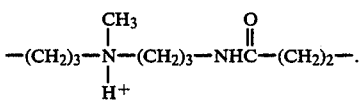

12. An improved immunoglobulin-solid phase reagent of the type wherein a carbohydrate moiety in the Fc region of the immunoglobulin is covalently attached to a solid phase support matrix through a hydrazone spacer arm, wherein the improvement comprises a hydrazone spacer arm of the formula:

wherein:
R₂ is a linear chain of at least six atoms, with at least one of said atoms being a tertiary amine which is protonated at a pH less than about eight, and the remaining atoms in the chain being carbon, oxygen, or nitrogen.

13. An improved reagent as in claim 12, wherein the solid phase support matrix is selected from the group consisting of agarose, dextran, cellulose, polymethacrylate, polystyrene, silica, protein, nucleic acid, and liposomes.

14. An improved reagent as in claim 13, wherein the solid phase support matrix is in the form of a bead, particulate, fiber, solid surface, membrane, or soluble polymer.

15. An improved reagent as in claim 12, wherein the linear chain includes an amide group separated by at least on carbon atom from the tertiary amine.

16. An improved reagent as in claim 15, wherein R₂ has the formula:

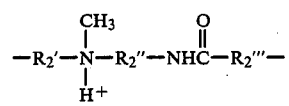

wherein:
R'₂, R''₂, and R'''₂ are aliphatic having from 1-6 atoms which may include from 0-2 primary or secondary nitrogen atoms.

17. An improved reagent as in claim 16 wherein R'₂, R''₂, and R'''₂ are selected from the group consisting of methylene, ethylene, propylene, and butylene.

18. An improved reagent as in claim 17, wherein R₂ is:

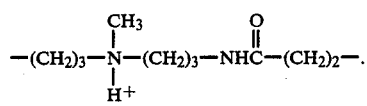

19. A method for conjugating proteins to solid phase support matrices and marker molecules, said method comprising:
introducing aldehyde functionalities to the protein; and
reacting the protein with a derivatized solid phase support matrix or marker molecule having a spacer arm terminating in a hydrazide functionality, wherein said spacer arm includes a chain of at least six atoms, with at least one of said atoms being a tertiary amine which is protonated at a pH less than about eight, and the remaining of said atoms being carbon, oxygen, or nitrogen.

20. A method as in claim 19, wherein the solid phase support matrix is selected from the group consisting of agarose, dextran, cellulose, polymethacrylate, polystyrene, silica, and liposomes.

21. A method as in claim 19, wherein the solid phase support matrix is in the form of a bead, particulate, fiber, solid surface, membrane, or soluble polymer.

22. A method as in claim 19, wherein the marker molecule is selected from the group consisting of enzymes, fluorescent compounds, bioluminescent compounds, nucleic acids, lectins, toxins, linker molecules, and chelating agents.

23. A method as in claim 19, wherein the protein is a glycoprotein, and the aldehyde is introduced by oxidizing a carbohydrate moiety on the glycoprotein.

24. A method as in claim 23, wherein the glycoprotein is an immunoglobulin.

25. A method as in claim 19, wherein the chain is linear and includes an amide group separated by at least one carbon atom from the tertiary amine.

26. A method as in claim 19, wherein $R_2$ has the formula:

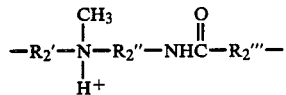

wherein:
$R'_2$, $R''_2$, and $R'''_2$ are aliphatic having from 1–6 atoms which may include from 0–2 primary or secondary nitrogen atoms.

27. A composition as in claim 26 wherein $R'_2$, $R''_2$, and $R'''_2$ are selected from the group consisting of methylene, ethylene, propylene, and butylene.

28. A composition as in claim 27, wherein $R_2$ is:

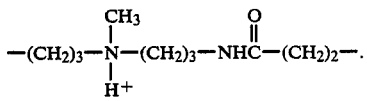

* * * * *